United States Patent
Green et al.

(10) Patent No.: US 6,977,302 B2
(45) Date of Patent: Dec. 20, 2005

(54) TRIAZOLE DERIVATIVES USEFUL IN THERAPY

(75) Inventors: Stuart Green, Sandwich (GB); Peter T. Stephenson, Sandwich (GB); Charles W. Murtiashaw, deceased, late of North Stonington, CT (US); by Martha H. Murtiashaw, legal representative, North Stonington, CT (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 57 days.

(21) Appl. No.: 10/810,100

(22) Filed: Mar. 26, 2004

(65) Prior Publication Data

US 2004/0236105 A1 Nov. 25, 2004

Related U.S. Application Data

(60) Division of application No. 10/339,087, filed on Jan. 9, 2003, now Pat. No. 6,790,957, which is a continuation-in-part of application No. 09/117,175, filed as application No. PCT/EP97/00445 on Jan. 27, 1997, now abandoned.

(30) Foreign Application Priority Data

Feb. 2, 1996 (GB) ............................................. 9602080

(51) Int. Cl.$^7$ .............................................. C07F 65/18
(52) U.S. Cl. ..................................................... 548/112
(58) Field of Search ......................................... 548/112

(56) References Cited

U.S. PATENT DOCUMENTS 4,952,232 A    8/1990   Cuomo et al.
5,278,175 A  * 1/1994   Kre et al. .................... 514/340
5,767,977 A  * 6/1998   Heeres et al. ................. 514/85

FOREIGN PATENT DOCUMENTS

| | | |
|---|---|---|
| EP | 0106807 A1 | 10/1983 |
| EP | 0413674 A2 | 8/1990 |
| EP | 0440372 A1 | 1/1991 |
| EP | 0472392 A2 | 8/1991 |
| EP | 0576201 A2 | 6/1993 |
| EP | 0567982 A1 | 11/1993 |
| EP | 0667346 A2 | 2/1995 |
| GB | 2099818 A | 4/1982 |
| WO | 9522973 | 8/1995 |
| WO | 9701552 | 1/1997 |

OTHER PUBLICATIONS

63–Pharmaceuticals, vol. 119, 1993, p. 525.

Maurin, et al. Int. J. Pharm., 1993, vol. 94, pp. 11–14.

* cited by examiner

*Primary Examiner*—Patricia L. Morris
(74) *Attorney, Agent, or Firm*—Peter C. Richardson; Bryan C. Zielinski; Elsa Djuardi

(57) ABSTRACT

The invention provides compounds of formula I, $$R^1\text{—OP(O)(OH)}_2 \qquad \qquad I$$

wherein $R^1$ represents the non-hydroxy portion of a triazole antifungal compound of the type comprising a tertiary hydroxy group; or a pharmaceutically acceptable sat thereof.

The compounds of the invention are useful in the treatment of fungal infections, and have good aqueous solubility.

3 Claims, No Drawings

TRIAZOLE DERIVATIVES USEFUL IN THERAPY

This application is a division of application Ser. No. 10/339,087, filed on Jan. 9, 2003, now U.S. Pat. No. 6,790,957, which is a continuation of application Ser. No. 09/117,175, filed on Jan. 8, 1999, now abandoned, which is a 371 of international application no. PCT/EP97/00445, filed on Jan. 27, 1997, now abandoned, which is published in English under International publication WO97/28169, and which claims priority from Great Britain application No. 9602080.5, filed on Feb. 2, 1996.

This invention relates to triazole derivatives useful in therapy (in particular in the treatment of fungal infections in humans and other mammals), methods for their use, formulations including them and processes for their production.

A large number of triazole antifungal compounds are known. For example, European Patent Application 0440372, Example 7, discloses (2R,3S)-2-(2,4-difluorophenyl)-3-(5-fluoro-4-pyrimidinyl)-1-(1H-1,2,4-triazol-1-yl)-butan-2-ol (also known as voriconazole) which has particularly good activity against the clinically important *Aspergillus* spp fungi. However, the compound has low solubility in aqueous media, necessitating the use of complexing agents to achieve satisfactory aqueous formulations, such as intravenous formulations. European Patent Application 0440372 suggests co-formulation with cyclodextrin derivatives to improve solubility; however, it is always desirable to keep the number of ingredients in a formulation to a minimum so as to minimize possible adverse reactions in patients.

UK Patent Application 2,128,193 discloses phosphoric acid esters for use as plant fungicides and insecticides.

It has now been found that triazole antifungal compounds of the type comprising a tertiary hydroxy group, including (2R,3S)-2-(2,4-difluorophenyl)-3-(5-fluoro-4-pyrimidinyl)-1-(1H-1,2,4-triazol-1-yl)-butan-2-ol, may be converted into pro-drugs having greatly enhanced solubility, but which are converted readily in vivo to give the desired active moiety.

According to the invention, there is provided a compound of formula I, $R^1$—OP(O)(OH)$_2$    I wherein $R^1$ represents the non-hydroxy portion of a triazole antifungal compound of the type comprising a tertiary hydroxy group;
or a pharmaceutically acceptable salt thereof.

The compounds of the invention are distinct from the prior art because the tertiary hydroxy group in triazole antifungal compounds of this type has not previously lent itself to functionalization.

Pharmaceutically acceptable salts that may be mentioned include alkali metal salts of the phosphate group, for example disodium or dipotassium salts; and salts with an amine counter ion, for example ethylenediamine, glycine or choline salts.

Preferably, $R^1$ represents a group of formula Ia,

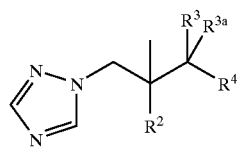

Ia in which
$R^2$ represents phenyl substituted by one or more halogen atoms;

$R^3$ represents H or CH$_3$;

$R^3$ represents H, or together with $R^3$ it may represent =CH$_2$; and $R^4$ represents a 5- or 6-membered nitrogen-containing heterocyclic ring which is optionally substituted by one or more groups selected from halogen, =O, phenyl [substituted by a group selected from CN and (C$_6$H$_4$)—OCH$_2$CF$_2$CHF$_2$] or CH=CH—(C$_6$H$_4$)—OCH$_2$CF$_2$CHF$_2$; or phenyl substituted by one or more groups selected from halogen and methylpyrazolyl.

When $R^1$ represents a group of formula Ia, as defined above, $R^2$ is preferably 2,4-difluorophenyl, and $R^3$ is preferably H or methyl.

Nitrogen-containing heterocyclic rings that $R^4$ may represent or comprise include triazolyl, pyrimidinyl and thiazolyl.

Preferred specific groups that $R^1$ may represent include:

(a)

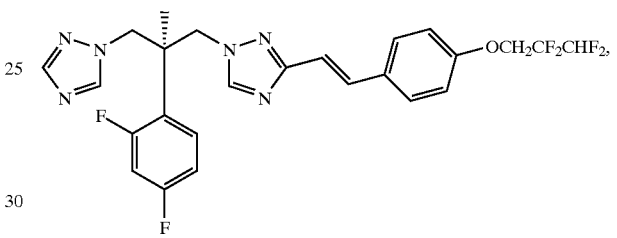

(b)

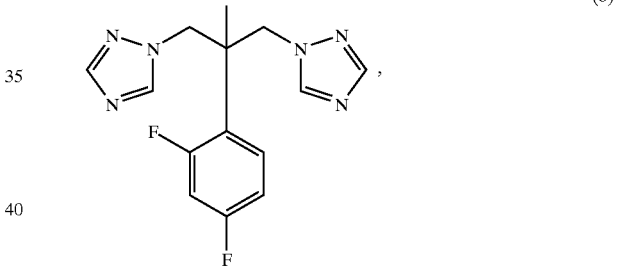

(c)

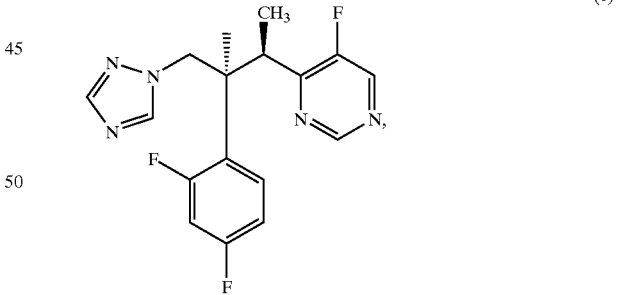

(d)

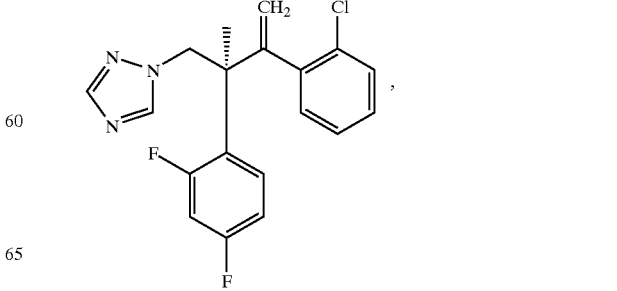

-continued

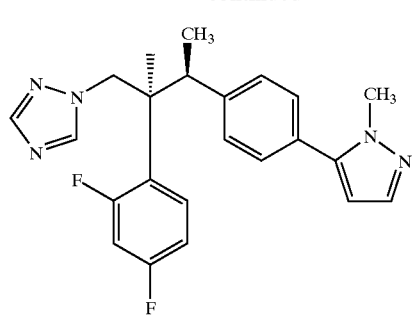

(e)

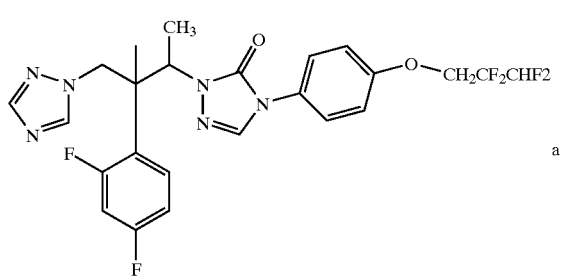

and (f)

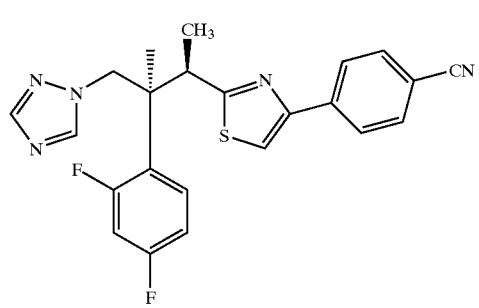

(g)

The triazole antifungal compounds corresponding to the groups (a)–(g) above are:

(a) D-0870 (under development by Zeneca, see also Example 19, European Patent Application 0472392); (b) fluconazole (sold by Pfizer, see also UK Patent Application 2099818); (c) Example 7 of European Patent Application 0440372, also known as voriconazole; (d) Example 35 of U.S. Pat. No. 4,952,232; (e) the compound of Example 8 of the present application; (f) Compound A of WO 95/22973 (see page 29), originally disclosed as Compound 30 in Example 27 of EP 567982; and (g) ER-30346 (see Drugs of the Future, 1996, 21(1): 20–24, Tetrahedron Letters, Vol 37, 45, pp 8117–8120, 1996 and European Patent Application 0667346, Example 88).

The present invention also provides a process for the production of a compound of formula I, as defined above, or a pharmaceutically acceptable salt thereof, which comprises phosphorylating a compound of formula II, $R^1OH$  II wherein $R^1$ is as defined above;
and where desired or necessary converting the resulting compound into a pharmaceutically acceptable salt or vice versa.

The phosphorylation may be carried out using the following steps (1)–(3):

(1) Reacting a compound of formula II, as defined above, with a compound of formula III, $R^aR^bN—P(OR^c)(OR^d)$  III wherein $R^a$ and $R^b$ independently represent $C_{1-6}$ alkyl, phenyl or substituted phenyl, or together with the nitrogen atom to which they are attached they may represent a ring such as a morpholine ring; and $R^c$ and $R^d$ independently represent hydroxy protecting groups; to give a phosphite compound of formula IV, $R^1—O—P(OR^c)(OR^d)$  IV wherein $R^1$, $R^c$ and $R^d$ are as defined above.

The reaction may be carried out in a solvent which does not adversely affect the reaction (e.g. methylene chloride) in the presence of a mild acid (for example tetrazole, 5-methyltetrazole or pyridinium hydrobromide) and optionally 4-dimethylaminopyridine, at room temperature or above.

(2) Reacting the resulting phosphite of formula IV with an oxidant (for example a peracid such as 3-chloroperoxybenzoic acid, or $H_2O_2$), to give a phosphate of formula V, $R^1—OP(O)(OR^c)(OR^d)$  V wherein $R^1$, $R^c$ and $R^d$ are as defined above. The reaction may be carried out in a solvent which does not adversely affect the reaction (e.g. methylene chloride or ethyl acetate) below room temperature (for example 0—-20° C.).

(3) Removing the hydroxy protecting groups from the compound of formula V to give a compound of formula I, as defined above.

As an alternative to step (1), phosphites of formula IV may be prepared according to steps (1A) and (1B):

(1A) Reaction of a compound of formula II, as defined above, with $PCl_3$ in the presence of a base to give a postulated intermediate compound of formula VI, $R^1—O—PCl_2$  VI wherein $R^1$ is as defined above. The reaction may be carried out in a solvent which does not adversely affect the reaction (e.g. methylene chloride or ethyl acetate) at a temperature in the range −20 to +20° C. (for example 0° C.). Suitable bases include pyridine and N-methylimidazole.

(1B) Reaction of the compound of formula VI with a compound of formula $R^cOH$ and/or $R^dOH$ (in which $R^c$ and $R^d$ are as defined above) to give a compound of formula IV, as defined above. The reaction is performed without isolation of the compound of formula VI, at a temperature around room temperature.

Hydroxy protecting groups which $R^c$ and $R^d$ may represent include benzyl optionally substituted by one or more halogen atoms (for example 2,6-dichlorobenzyl or 2-chloro-6-fluorobenzyl), or $C_{1-6}$ alkyl such as t-butyl. Benzyl groups may be removed using catalytic hydrogenation (e.g. over Pearlman's catalyst or palladium-on-carbon) or bromotrimethylsilane, and $C_{1-6}$ alkyl groups may be removed using hydrolytic conditions.

When $R^c$ and $R^d$ represent benzyl or substituted benzyl, if step (3) is carried out in the presence of sodium acetate or sodium hydroxide, the disodium salt may be obtained directly.

Compounds of formulae II and III are either known or are available using known techniques.

It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc, 1991.

The compounds of the invention are useful because they possess pharmacological activity in animals, including humans. In particular, the compounds are useful in the treatment or prevention of fungal infections. For example, they are useful in treating topical fungal infections in man caused by, among other organisms, species of *Candida, Trichophyton, Microsporum* or *Epidermophyton,* or in mucosal infections caused by *Candida albicans* (e.g. thrush and vaginal candidiasis). They can also be used in the treatment of systemic fungal infections caused by, for example, species of *Candida* (e.g. *Candida albicans*), *Cryptococcus neoformans, Aspergillus flavus, Aspergillus fumigatus, Coccidoides, Paracoccidiodes, Histoplasma* or *Blastomyces.*

Thus, according to another aspect of the invention, there is provided a method of treatment or prevention of a fungal infection which comprises administering a therapeutically effective amount of a compound of the invention to a patient. The use of the compounds of the invention as pharmaceuticals, and the use of the compounds of the invention in the manufacture of a medicament for the treatment or prevention of fungal infections are also provided.

The in vitro evaluation of the antifungal activities of the compounds of the invention can be performed by determining the minimum inhibitory concentration (m.i.c.), which is the concentration of the test compounds, in a suitable medium, at which growth of the particular micro-organism fails to occur. In practice, a series of agar plates, each having the test compound incorporated at a particular concentration, is inoculated with a standard culture of, for example, *Candida albicans*, and each plate is then incubated for 48 hours at 37° C. The plates are then examined for the presence or absence of growth of the fungus and the appropriate m.i.c. value is noted. Other micro-organisms used in such tests can include *Aspergillus fumigatus, Trichophyton* spp., *Microsporum* spp., *Epidermophyton floccosum, Coccidioides immitis* and *Torulopsis glabrata.*

Some compounds of the invention, although active in vivo, may not demonstrate activity in these in vitro tests.

The in vivo evaluation of the compounds of the invention can be carried out at a series of dose levels by intraperitoneal or intravenous injection, or by oral administration, to mice which are inoculated with, e.g. a strain of *Candida albicans* or *Aspergillus fumigatus.* Activity is based on the survival of a treated group of mice after the death of an untreated group of mice. The dose level at which the compound provides 50% protection against the lethal effect of the infection ($PD_{50}$) is noted. For *Aspergillus* spp. infection models, the number of mice cured of the infection after a set dose allows further assessment of activity.

For human use, the compounds of the invention can be administered alone, but will generally be administered in admixture with a pharmaceutically acceptable carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the invention will be from 0.01 to 20 mg/kg (in single or divided doses) when administered by either the oral or parenteral route. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the invention can be administered in the form of a suppository or pessary, or they may be applied topically in the form of a lotion, solution, cream (for example comprising an aqueous emulsion of polyethylene glycols or liquid paraffin); or they can be incorporated, at a concentration between 1 and 10%, into an ointment consisting of a white wax or white soft paraffin base together with such stabilizers and preservatives as may be required.

Thus, according to another aspect of the invention, there is provided a pharmaceutical formulation including preferably less than 50% by weight of a compound of the invention in admixture with a pharmaceutically acceptable adjuvant, diluent or carrier. Aqueous intravenous formulations are of particular interest.

The invention is illustrated by the following Examples.

EXAMPLE 1

1-(2,4-Difluorophenyl)-1,3-bis(1H-1,2,4-triazol-1-yl)-2-propyl dihydrogen phosphate (a) Dibenzyl 2-(2,4-difluorophenyl)-1,3-bis(1H-1,2,4-triazol-1-yl)-2-propyl phosphate Method A

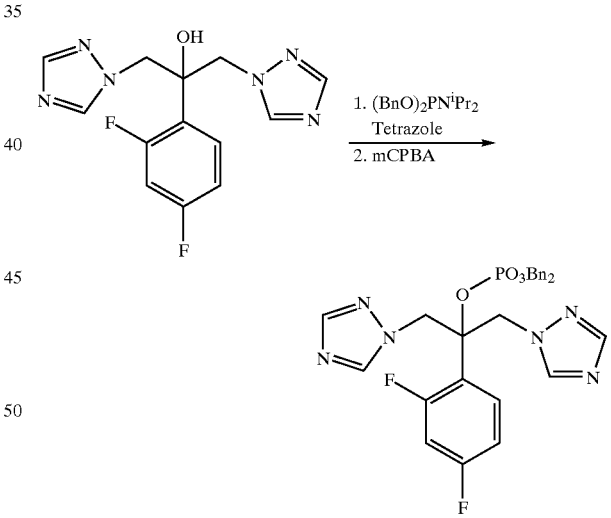

A solution of 2-(2,4-difluorophenyl)-1,3-bis(1H-1,2,4-triazol-1-yl)propan-2-ol (also known as fluconazole, 10.0 g, 32.6 mmol), 1H-tetrazole (6.85 g, 97.8 mmol), dibenzyl diisopropyl phosphoramidite (22.55 g, 65.2 mmol) in methylene chloride (100 ml) was stirred at room temperature under a nitrogen atmosphere for 2 hours. The mixture was then cooled to 0° C., and a solution of 3-chloroperoxybenzoic acid (13.5 g, 50-55% w/w, 39.1 mmol) in methylene chloride (50 ml) was added maintaining the temperature at 0° C. The resulting mixture was allowed to warm to room temperature for 1 hour before washing with aqueous sodium metabisulphite and sodium bicarbonate.

After drying (MgSO$_4$) the solvent was removed and replaced with methyl isobutyl ketone (37 ml) and tert-butyl methyl ether (74 ml). After granulating at −10° C. for 1 hour the product was filtered and washed with ice cold methyl isobutyl ketone and tert-butyl methyl ether (1:3, 15 ml) and dried at 50° C. under vacuum for 18 hours to give the subtitle compound (16.05 g, 87%), m.p. 93° C.

Found: C, 57.12; H, 4.46; N, 14.85. C$_{27}$H$_{25}$F$_2$N$_6$O$_4$P requires C, 57.24; H, 4.46; N, 14.84%. m/z 567 (MH$^+$) $^1$H NMR (300 MHz, CDCl$_3$) δ=4.90 (d, 2H), 4.95 (d, 2H), 5.05 (d, 2H), 5.19 (d, 2H), 6.58–6.73 (m, 2H), 6.88–6.95 (m, 1H), 7.20–7.30 (m, 4H) 7.32–7.38 (m; 6H), 7.80 (s, 2H), 8.36 (s, 2H).

Method B

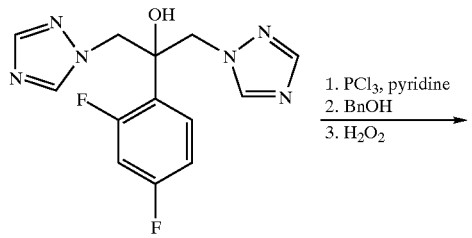

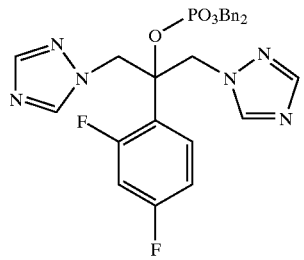

To stirred ethyl acetate (1530 ml) was added 2-(2,4-difluorophenyl)-1,3-bis(1H-1,2,4-triazol-1-yl)propan-2-ol (also known as fluconazole, 306 g, 1.00 mol) and pyridine (237.3 g, 3.00 mol) before cooling to 0° C. Phosphorus trichloride (137.4 g, 1.00 mol) was added dropwise to the reaction mixture maintaining the temperature between 0–5° C. before allowing the reaction mixture to warm to 15° C. over 30 minutes. Benzyl alcohol (216 g, 2.00 mol) was then added over 30 minutes at 15–20° C. After a further 30 minutes hydrogen peroxide (27.5% w/w in water, 373 g) was added maintaining the temperature at 15–20° C. After 30 minutes the aqueous phase was removed and the organic phase washed with aqueous sodium metabisulphite, dilute hydrochloric acid and water. The solvent was removed at reduced pressure and replaced with methyl isobutyl ketone (850 ml) and tert-butyl methyl ether (1132 ml). After granulating at 20° C. for 1 hour and at 0° C. for 1 hour, the product was filtered and washed with ice cold tert-butyl methyl ether (2×220 ml) and dried at 50° C. under vacuum for 18 hours to give the subtitle compound (358 g, 63%). The melting point and spectroscopic data was identical to that stated in method A.

(b) 2-(2,4-Difluorophenyl)-1,3-bis(1H-1,2,4-triazol-1-yl)-2-propyl dihydrogen phosphate

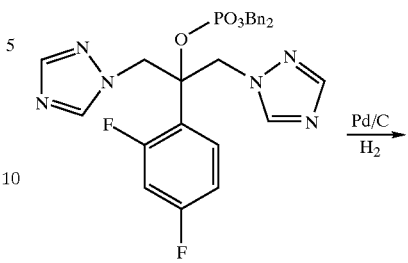

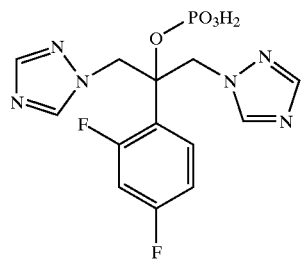

A slurry of the compound of step (a) (9.80 g, 17.3 mmol), 5% palladium on carbon catalyst (50% wet, 1.0 g) and sodium hydroxide (1.38 g, 34.6 mmol) in water (26 ml) was hydrogenated at room temperature and 414 kPa (60 p.s.i.) for 20 hours. The solution was filtered through a pad of celite (trade mark) and washed with water (5 ml). The toluene was separated and the aqueous phase cooled to 0° C. whereupon sulphuric acid (1.70 g, 17.3 mmol) was added. The resulting slurry was granulated at 0° C. for 1 hour and then filtered, washed with water (2×5 ml) and dried under vacuum at 50° C. to give the title compound (5.80 g, 87%). m.p. 223–224° C.

Found: C, 40.28; H, 3.39; N, 21.63. C$_{13}$H$_{13}$F$_2$N$_6$O$_4$P requires C, 40.43; H, 3.39; N, 21.76%. $^1$H NMR (300 MHz, DMSO) δ=5.07 (d, 2H) 5.24 (d, 2H), 6.77–6.83 (m, 1H), 7.00–7.18 (m, 2H), 7.75 (s, 2H), 8.53 (s, 2H).

EXAMPLE 2

2-(2,4-Difluorophenyl)-1,3-bis(1H-1,2,4-triazol-1-yl)-2-propyl disodium phosphate

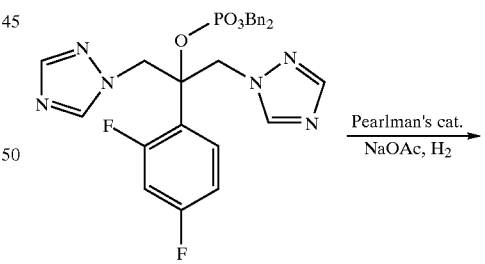

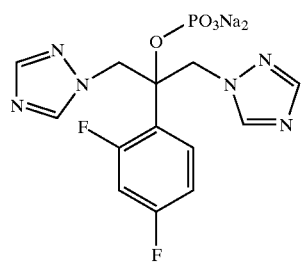

A solution of the compound of Example 1(a) (10.0 g, 17.7 mmol) and sodium acetate (2.90 g, 35.3 mmol) in ethanol (160 ml) and water (20 ml) was hydrogenated over Pearlman's catalyst (1.00 g) at room temperature and at 345 kPa (50 p.s.i.) for 16 hours. The solution was filtered through a pad of celite (trade mark) and the solvents removed at reduced pressure to leave a thick syrup. This was dissolved in ethanol (100 ml) with the aid of sonication and warmed to reflux. The resulting solution was allowed to cool slowly and granulate for 1 hour at room temperature. The product was filtered, washed with ethanol (10 ml) and dried under vacuum at 50° C. to give the title compound (4.48 g, 59%). m.p. 160–162° C.

$^1$H NMR (300 MHz, $D_2O$) δ=5.01 (d, 2H), 5.40 (d, 2H), 6.60 (m, 1H), 6.79 (m, 1H), 7.11 (m, 1H), 7.63 (s, 2H), 8.68 (s, 2H).

EXAMPLE 3

(2R,3S)-2-(2,4-Difluorophenyl)-3-(5-fluoro-4-pyrimidinyl)-1-(1H-1,2,4-triazol-1-yl)-2-butyl dihydrogen phosphate (a) Dibenzyl (2R,3S)-2-(2,4-difluorophenyl)-3-(5-fluoro-4-pyrimidinyl)-1-(1H-1,2,4-triazol-1-yl)-2-butyl phosphate

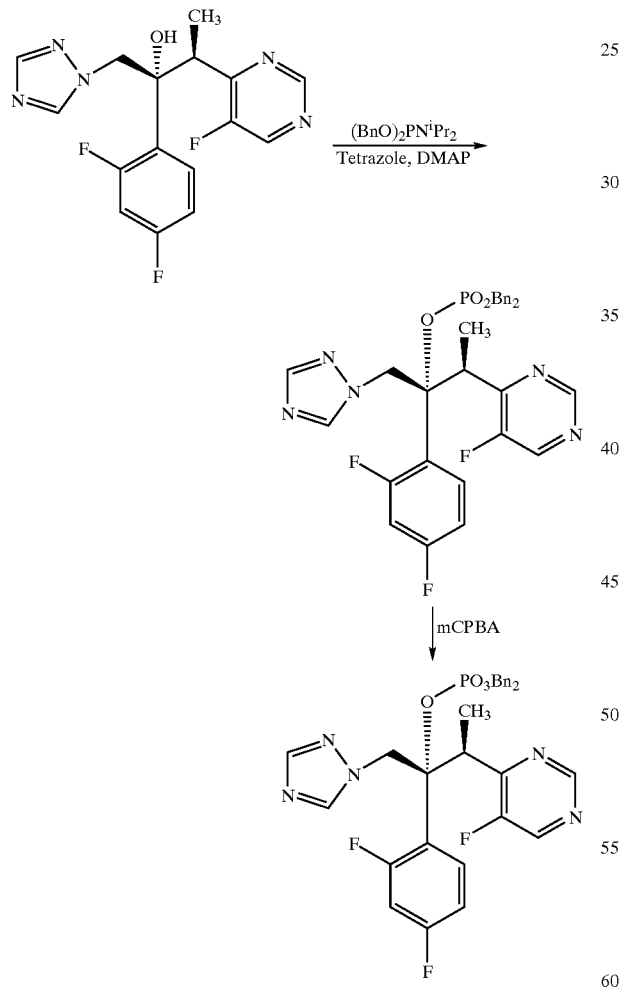

A solution of (2R,3S)-2-(2,4-difluorophenyl)-3-(5-fluoro-4-pyrimidinyl)-1-(1H-1,2,4-triazol-1-yl)butan-2-ol (the compound of Example 7, EP 0440372, also known as voriconazole, 17.0 g, 48.7 mmol), 4-dimethylaminopyridine (10.2 g, 83.5 mmol) 10.2 g, 146 mmol) and dibenzyl diisopropylphosphoramidite (33.6 g, 97.4 mmol) in methylene chloride (100 ml) was stirred at reflux for 2 hours and a further 16 hours at room temperature under a nitrogen atmosphere. The reaction mixture was then washed with hydrochloric acid and then sodium bicarbonate, dried ($MgSO_4$) and concentrated. The crude product phosphite was purified by column chromatography (silica gel, 300 g, eluting with 3:1 to 1:1 hexane:ethyl acetate gradient) to give a pale yellow oil. This was dissolved in methylene chloride (100 ml) and cooled to −10° C., whereupon a solution of 3-chloroperoxybenzoic acid (14.8 g, 57% w/w, 48.9 mmol) in methylene chloride (100 ml) was added maintaining the temperature below 0° C. The resulting mixture was allowed to warm to room temperature for 10 minutes before washing with aqueous sodium metabisulphite and sodium bicarbonate. After drying ($MgSO_4$) and concentrating the crude product was purified by column chromatography (silica gel, 300 g, eluting with ethyl acetate) to give the subtitle compound as a viscous syrup (17.86 g, 60%).

m/z 610 ($MH^+$) $^1$H NMR (300 MHz, $CDCl_3$) δ=1.39 (d, 3H), 4.41 (q, 1H), 4.79 (d, 2H), 4.96 (d, 2H), 5.34 (d, 1H), 5.40 (d, 1H), 6.59–6.66 (m, 1H), 6.72–6.82 (m, 1H), 7.02–7.18 (m, 3H), 7.23–7.37 (m, 8H), 7.79 (s, 1H), 8.46 (d, 1H), 8.52 (s, 1H), 8.90 (d, 1H).

(b) (2R,3S)-2-(2,4-Difluorophenyl)-3-(5-fluoro-4-pyrimidinyl)-1-(1H-1,2,4-triazol-1-yl)-2-butyl dihydrogen phosphate

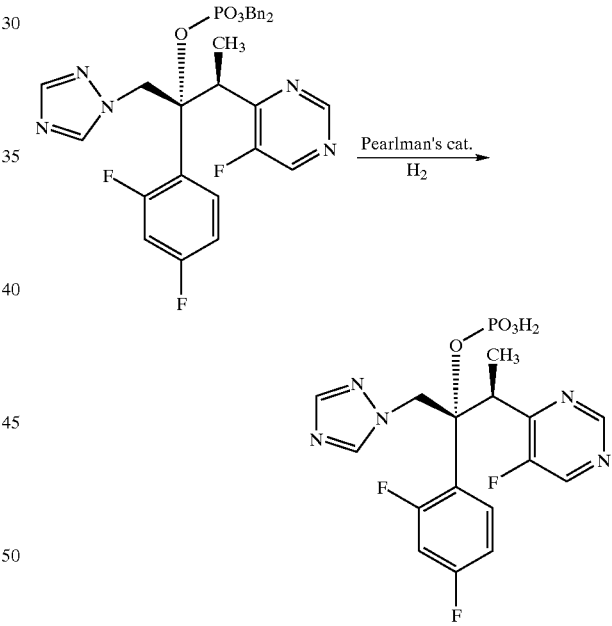

A solution of the compound of step (a) (5.0 g, 8.83 mmol) in methanol (100 ml) was hydrogenated over Pearlman's catalyst (1.0 g) at room temperature and at 414 kPa (60 p.s.i.) for 16 hours. The solution was filtered through a pad of celite (trade mark) and concentrated. The crude product was redissolved in hot methanol (20 ml) and granulated at 0° C. for 1 hour. After filtering and washing with methanol (5 ml) the product was dried under vacuum at 50° C. to give the title compound (1.72 g, 49%). m.p. 145–145° C.

$^1$H NMR (300 MHz, DMSO) δ=1.31 (d, 3H), 4.01 (q, 1H), 5.31 (d, 1H), 5.42 (d, 1H), 6.90–6.97 (m, 1H), 7.04–7.14 (m, 1H), 7.20–7.30 (m, 1H), 7.95 (s, 1H), 8.70 (d, 1H), 8.73 (s, 1H), 8.89 (d, 1H).

EXAMPLE 4

(2R,3S)-2-(2,4-Difluorophenyl)-3-(5-fluoro-4-pyrimidinyl)-1-(1H-1,2,4-triazol-1-yl)-2-butyl dihydrogen phosphate (Alternative Preparation)

(a) Bis(2-chloro-6-fluorobenzyl) (2R,3S)-2-(2,4-difluorophenyl)-3-(5-fluoro-4-pyrimidinyl)-1-(1H-1,2,4-triazol-1-yl)-2-butyl phosphate

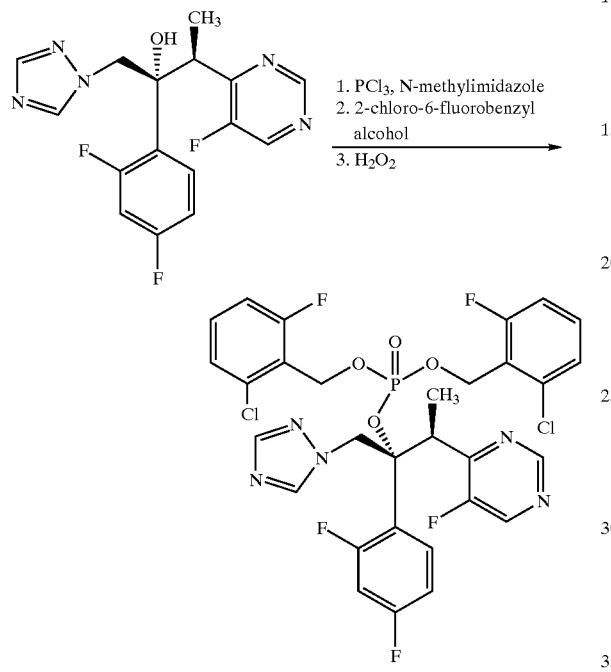

A solution of (2R,3S)-2-(2,4-difluorophenyl)-3-(5-fluoro-4-pyrimidinyl)-1-(1H-1,2,4-triazol-1-yl)butan-2-ol (the compound of Example 7, EP 0440372, also known as voriconazole, 10.0 g, 28.6 mmol) and 1-methylimidazole (9.40 g, 114 mmol) in methylene chloride (30 ml) was cooled to 0° C. whereupon a solution of phosphorus trichloride (4.73 g, 34.4 mmol) in methylene chloride (20 ml) was added, maintaining the temperature below 10° C. After 15 minutes a solution of 2-chloro-6-fluorobenzyl alcohol (12.0 g, 74.4 mmol) in methylene chloride (40 ml) was added at between 0–10° C. After 30 minutes, hydrogen peroxide (25 ml, 30% solution in water) was added dropwise maintaining the temperature below 20° C. with cooling. After a further 1 hour the reaction mixture was separated and the organic phase was washed with water (2×100 ml), dried (MgSO$_4$) and concentrated. The resulting viscous oil was granulated with tert-butyl methyl ether (60 ml) for 2 hours at 0° C. The product was filtered, washed with tert-butyl methyl ether (20 ml) and dried at 50° C. in vacuo for 18 hours to give the subtitle compound as a white crystalline solid (18.1 g, 88% yield), m.p. 140–141° C.

$^1$H NMR (300 MHz, CDCl$_3$) δ=1.39 (d, 3H), 4.33 (q, 1H), 5.08 (d, 1H), 5.13 (d, 1H), 5.27 (d, 1H), 5.31 (d, 1H), 5.32 (d, 1H), 5.42 (d, 1H), 6.60–6.75 (m, 2H), 6.92–7.07 (m, 2H), 7.11–7.37 (m, 5H), 7.81 (s, 1H), 8.44 (d, 1H), 8.61 (s, 1H), 8.91 (s, 1H).

(b) (2R,3S)-2-(2,4-Difluorophenyl)-3-(5-fluoro-4-pyrimidinyl)-1-(1H-1,2,4-triazol-1-yl)-2-butyl dihydrogen phosphate

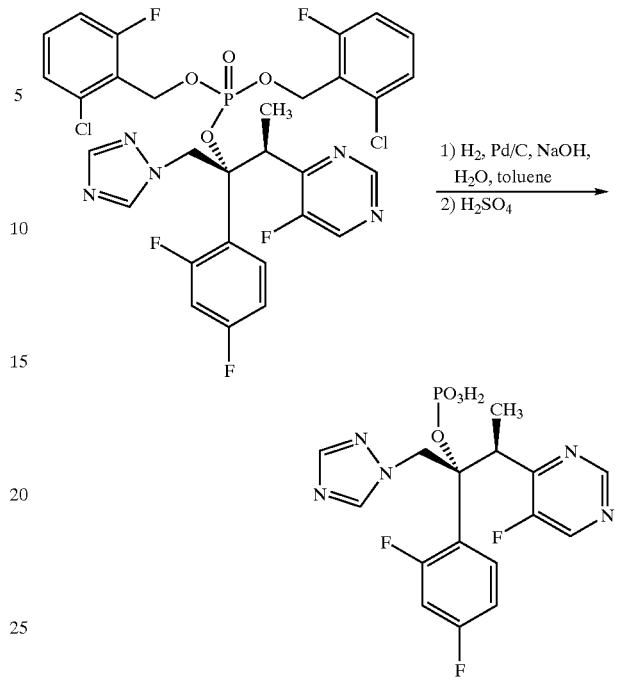

A mixture of the compound of step (a) (50 g, 70 mmol), sodium hydroxide (8.40 g, 210 mmol) and 5% palladium on carbon catalyst (10 g) in toluene (450 ml) and water (150 ml) was hydrogenated at room temperature and 414 kPa (60 p.s.i.) for 24 hours. The reaction mixture was filtered through celite (trade mark) and the toluene layer separated and discarded. The aqueous layer was then washed with methylene chloride (2×75 ml) and toluene (2×75 ml) and then cooled to 0° C. whereupon sulphuric acid (10.3 g, 105 mmol) was added. After granulating at 0° C. for 1 hour the product was filtered, washed with water (60 ml) and dried under vacuum at 50° C. for 16 hours to give the title compound (20.5 g, 68%). The proton NMR data was identical to that obtained in Example 3(b).

Found: C, 44.48; H, 3.45; N, 16.19. C$_{16}$H$_{15}$F$_3$N$_5$O$_4$O requires C, 44.77; H, 3.52; N, 16.31%.

EXAMPLE 5

(2R,3S)-2-(2,4-Difluorophenyl)-3-(5-fluoro-4-pyrimidinyl)-1-(1H-1,2,4-triazol-1-yl)-2-butyl (2-hydroxyethyl)trimethylammonium hydrogen phosphate dihydrate

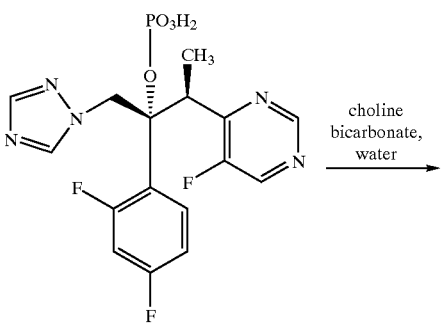

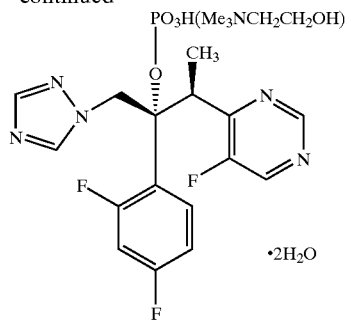

To a stirred slurry of the compound of Example 3(b) (214.7 g, 500 mmol) in acetone (2070 ml) was added a solution of choline bicarbonate (75% w/w in water, 110 g, 500 mmol) over 10 minutes. The slurry was warmed to reflux for 20 minutes, filtered through a pad of celite (trade mark) to remove any insoluble material then cooled to 20° C. and granulated for 1 hour. The resulting product was collected by filtration, washed with acetone (2×250 ml) and dried at 20° C. under vacuum for 18 hours to give the title compound (233.3 g, 74%) m.p. 114–115° C.

$^1$H NMR (300 MHz, DMSO) δ=1.23 (d, 3H), 3.07 (s, 9H), 3.38 (t, 2H), 3.60 (q, 1H), 3.78 (q, 2H), 5.50 (s, 2H), 6.72–6.80 (m, 1H), 6.94–7.02 (m, 1H), 7.36–7.42 (m, 1H), 7.82 (s, 1H), 8.59 (d, 1H), 8.78 (d, 1H), 9.35 (s, 1H).

EXAMPLE 6

2-(2,4-Difluorophenyl)-1-{3-[(E)-4-(2,2,3,3-tetrafluoropropoxy)styryl]-1H-1,2,4-triazol-1-yl}-3-(1H-1,2,4-triazol-1-yl)-2-propyl dihydrogen phosphate (a) Dibenzyl 2-(2,4-difluorophenyl)-1-{3-[(E)-4-(2,2,3,3-tetrafluoropropoxy)styryl]-1H-1,2,4-triazol-1-yl}-3-(1H-1,2,4-triazol-1-yl)-2-propyl phosphate

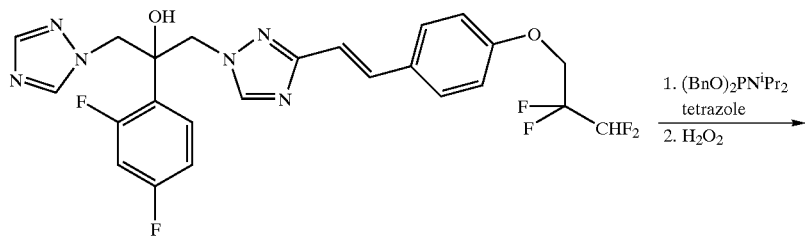

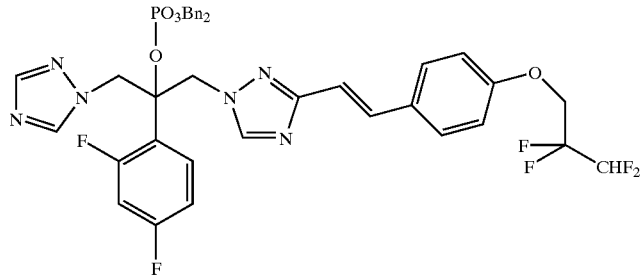

2-(2,4-Difluorophenyl)-1-{3-[(E)-4-(2,2,3,3-tetrafluoropropoxy)styryl]-1H-1,2,4-triazol-1-yl}-3-(1H-1,2,4-triazol-1-yl)propan-2-ol (the racemate of Example 19, EP 0472392, 475 mg, 0.88 mmol), 1H-tetrazole (185 mg, 2.64 mmol) and dibenzyl diisopropylphosphoramidite (607 mg, 1.76 mmol) in methylene chloride (5 ml) was stirred at room temperature under a nitrogen atmosphere for 20 hours. The mixture was then cooled to 0° C., and hydrogen peroxide (1.0 ml, 30% solution in water) was added dropwise maintaining the temperature below 20° C. The resulting mixture was stirred at 20° C. for 30 minutes before separating the organic layer, which was washed with water, dried (MgSO$_4$) and the solvent evaporated. The resulting pale yellow oil was purified by column chromatography (silica gel, eluting with ethyl acetate/hexane) to give the subtitle compound as a viscous syrup (595 mg, 84%).

$^1$H NMR (300 MHz, CDCl$_3$) δ=4.37 (t, 2H), 4.91 (d, 2H), 4.97 (d, 2H), 5.02 (d, 1H), 5.07 (d, 1H), 5.16 (d, 1H), 5.18 (d, 1H), 6.05 (tt, 1H), 6.59–6.78 (m, 2H), 6.82 (d, 1H), 6.90 (d, 2H), 6.91–7.00 (m, 1H), 7.21–7.38 (m, 10H), 7.42 (d, 2H), 7.42 (d, 1H), 7.79 (s, 1H), 8.28 (s, 1H), 8.39 (s, 1H).

(b) 2-(2,4-Difluorophenyl)-1-{3-[(E)-4-(2,2,3,3-tetrafluoroproroxy)styryl]-1H-1,2,4-triazol-1-yl}-3-(1H-1,2,4-triazol-1-yl)-2-propyl dihydrogen phosphate

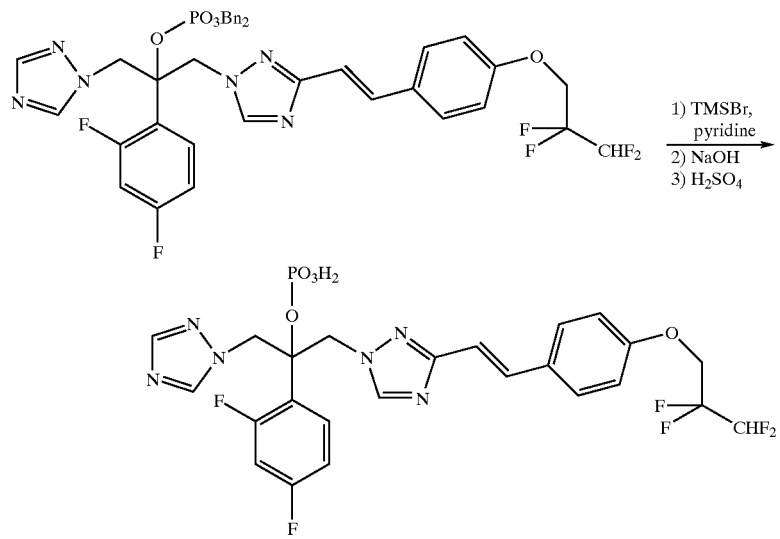

A solution of the compound of step (a) (298 mg, 0.37 mmol) in methylene chloride (5 ml) was cooled to 1° C. and then treated with bromotrimethylsilane (254 mg, 1.66 mmol) and pyridine (180 mg, 3.10 mmol). The resulting mixture was stirred at 0° C. for 3 hours and then quenched with water (1 ml) containing sodium hydroxide (96 mg, 2.41 mmol). The mixture was then acidified with dilute sulphuric acid and the product extracted into ethyl acetate. After washing with brine, the ethyl acetate phase was dried (MgSO$_4$) and the solvent evaporated to give the title compound as a pale yellow foam (202 mg, 88%).

EXAMPLE 7

(2RS,3RS)-3-(4-[4-Cyanophenyl]thiazol-2-yl)-2-(2,4-difluorophenyl)-1-(1H-1,2,4-triazol-1-yl)-2-butyl dihydrogen phosphate (a) (2RS,3RS)-3-(4-[4-cyanophenyl]thiazol-2-yl)-2-(2,4-difluorophenyl)-1-(1H-1,2,4-triazol-1-yl)-2-butyl phosphate

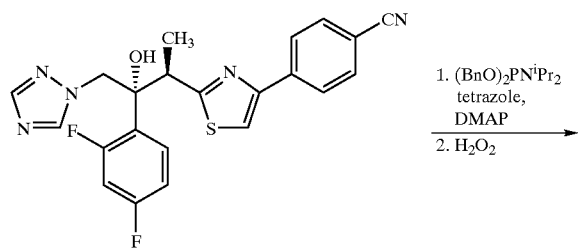

3-[4-(4-Cyanophenyl)thiazol-2-yl]-2-(2,4-difluorophenyl)-1-(1H-1,2,4-triazol-1-yl)butan-2-ol (Example 88, EP 0667346, 900 mg, 2.06 mmol), 1H-tetrazole (432 mg, 6.18 mmol), 4-dimethylaminopyridine (100 mg, 0.82 mmol) and dibenzyl diisopropylphosphoramidite (1.42 g, 4.12 mmol) in methylene chloride (10 ml) were refluxed under a nitrogen atmosphere for 20 hours. The mixture was then cooled to 1° C., and hydrogen peroxide (2.5 ml, 30% solution in water) was added dropwise maintaining the temperature below 20° C. The resulting mixture was stirred at 20° C. for 30 minutes before separating the organic layer, which was washed with water, dried (MgSO$_4$) and the solvent evaporated. The resulting pale yellow oil was purified by column chromatography (silica gel, eluting with ethyl acetate/hexane) to give the subtitle compound as a viscous syrup (722 mg, 51%).

$^1$H NMR (300 MHz, CDCl$_3$) δ=1.40 (d, 3H), 4.38 (q, 1H), 4.81–4.96 (m, 4H), 5.40 (d, 1H), 5.43 (d, 1H), 6.62–6.71 (m, 1H), 6.74–6.82 (m, 1H), 7.15–7.37 (m, 10H), 7.58 (s, 1H), 7.62 (d, 2H), 7.73 (s, 1H), 7.97 (d, 2H), 8.48 (s, 1H).

(b) (2RS,3RS)-3-(4-[4-Cyanophenyl]thiazol-2-yl)-2-(2,4-difluorophenyl)-1-(1H-1,2,4-triazol-1-yl)-2-butyl dihydrogen phosphate

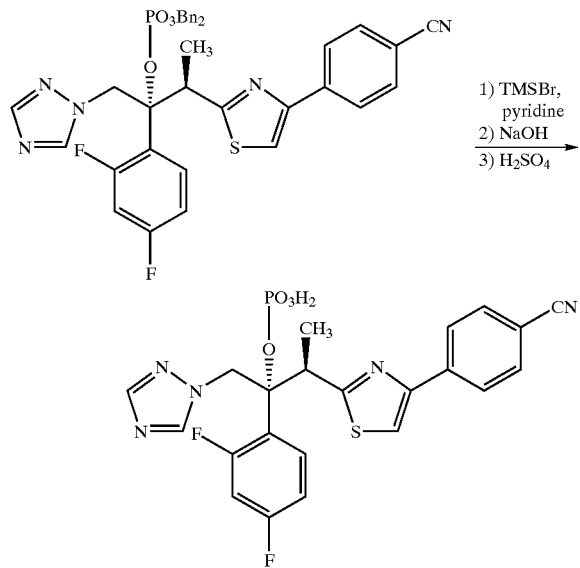

A solution of the compound of step (a) (310 mg, 0.44 mmol) in methylene chloride (5 ml) was cooled to 0° C. and then treated with bromotrimethylsilane (303 mg, 1.98 mmol) and pyridine (215 mg, 3.70 mmol). The resulting mixture was stirred at 0° C. for 3 hours and then quenched with water (1 ml) containing sodium hydroxide (115 mg, 2.87 mmol). A yellow precipitate was formed, which was isolated by filtration and then partitioned between dilute sulphuric acid and methylene chloride. The organic phase was washed with brine, dried (MgSO$_4$) and the solvent evaporated to give the title compound as a pale yellow solid (80 mg, 35%).

$^1$H NMR (300 MHz, DMSO) δ=1.38 (d, 3H), 4.22 (q, 1H), 5.37 (d, 1H), 5.41 (d, 1H), 6.88–6.97 (m, 1H), 7.09–7.19 (m, 1H), 7.31–7.40 (m, 1H), 7.80 (s, 1H), 7.87 (d, 2H), 8.05 (d, 2H), 8.32 (s, 1H), 8.65 (s, 1H).

EXAMPLE 8

(2R,3S)-2-(2,4-Difluorophenyl)-3-[4-(1-methylpyrazol-5-yl)phenyl-1-(1,2,4-triazol-1-yl)-2-butyl disodium phosphate a) O,N-dimethyl-4-iodobenzenehydroxamic acid A solution of pyridine (104 g, 1.32 mol) in dichloromethane (150 ml) was added dropwise to a suspension of 4-iodobenzoyl chloride (251 g, 0.94 mol) and N,O-dimethylhydroxylamine hydrochloride (97 g, 0.94 mol) in dichloromethane (850 ml) at 0° C. The mixture was allowed to warm to room temperature and was stirred for 18 hours. The solution was evaporated under reduced pressure, the residue was dissolved in ethyl acetate (1 l), and was then washed with dilute hydrochloric acid (2N, 3×400 ml) and saturated sodium bicarbonate solution (300 ml) and dried (Na$_2$SO$_4$). The organic extract was evaporated under reduced pressure. The residue was purified by distillation to yield the subtitle compound (241 g, 93%) as a yellow oil, b.p. 130° C. (0.1 mm Hg), which was characterized by $^1$H NMR.

(b) 2-(2,4-Difluorophenyl)-1-(4-iodophenyl)ethanone 2,4-Difluorobenzyl bromide (23.7 ml, 0.114 mol) was added dropwise to a stirred mixture of magnesium turnings (8.1 g, 0.183 mol) in dry ether (300 ml) under nitrogen. The mixture was warmed initially until reaction started, and thereafter the bromide was added at such a rate as to maintain a gentle reflux. After 1 hour, the resulting solution of the Grignard reagent was added dropwise at −78° C. to a solution of O,N-dimethyl-4-iodobenzenehydroxamic acid [see step (a)] (45.7 g, 0.157 mol) in dry ether (300 ml), and the mixture was allowed to warm slowly to room temperature overnight. The mixture was partitioned between saturated aqueous ammonium chloride and ethyl acetate, and the organic solution was separated, dried (MgSO$_4$) and concentrated under reduced pressure, to give the title compound as a white solid, 38.71 g (69%), which was characterised by $^1$H-N.M.R. spectroscopy.

(c) 2-(2,4-Difluorophenyl)-1-(4-iodophenyl)prop-2-enone

Bis(dimethylamino)methane (8.78 ml, 0.075 mol) was added dropwise to a stirred suspension of 2-(2,4-difluorophenyl)-1-(4-iodophenyl)ethanone [17.73 g, 0.04595 mol, from step (b)] in acetic anhydride (23.1 ml, 0.248 mol) at room temperature. There was an exothermic reaction, and the temperature of the mixture rose to 60° C. After the end of the addition, the mixture was stirred at room temperature for 35 minutes, and then iced water was added to hydrolyse the excess acetic anhydride. After a further 30 minutes, the product was extracted into ethyl acetate, and the extracts were washed with dilute hydrochloric acid, saturated aqueous sodium bicarbonate, dried (MgSO$_4$), and concentrated under reduced pressure, to give the title compound as a white solid (17.03 g, 93%), which was characterised by $^1$H-N.M.R. spectroscopy.

(d) 2-(2,4-Difluorophenyl)-2-(4-iodobenzoyl)oxirane

Benzyltrimethylammonium hydroxide (3.44 ml, 40% aqueous solution, 8.2 mmol) was added in one portion to a solution of 2-(2,4-difluorophenyl)-1-(4-iodophenyl)prop-2-enone [37.3 g, 100.8 mmol, from step (c)] and t-butylhydroperoxide (36.6 ml, 3M in trimethylpentane, 109 mmol) in toluene (550 ml) at room temperature. After 2 hours, the mixture was washed with water (2×500 ml), dried (MgSO$_4$) and concentrated under reduced pressure to give the title compound as a white solid (37.46 g, 96%), which was characterised by $^1$H-N.M.R. spectroscopy.

(e) (2,4-Difluorophenyl)-2-[1-(4-iodophenyl)-ethenyl]oxirane n-Butyllithium (50 ml, 2.5 M in hexane, 125 mmol) was added dropwise over 10 minutes to a stirred suspension of methyltriphenylphosphonium bromide (45.0 g, 126 mmol) in dry THF (600 ml) under nitrogen at −70° C. The mixture was allowed to warm to −20° C., over 20 minutes, then a solution of 2-(2,4-difluorophenyl)-2-(4-iodobenzoyl) oxirane [37.46 g, 97 mmol, from step (d)] in dry THF (200 ml) was added over 5 minutes. The mixture was allowed to warm to room temperature and stirred for 84 hours. 10% Aqueous ammonium chloride (500 ml) was added, and the mixture was concentrated under reduced pressure. The product was extracted into ethyl acetate and the combined extracts were dried (MgSO4) and concentrated under reduced pressure. The solid residue was treated with boiling hexane (3×500 ml), and the residual solid discarded. The hexane solutions were combined, filtered through a short pad of silica gel, and concentrated under reduced pressure to give the title compound as a yellow oil (34.3 g, 92%), which was characterised by $^1$H-N.M.R. spectroscopy.

(f) 2-(2,4-Difluorophenyl)-3-(4-iodophenyl)-1-(1H-1,2,4-triazol-1-yl)-3-buten-2-ol Sodium 1,2,4-triazole (12.15 g, 133 mmol) was added to a solution of (2,4-difluorophenyl)-2-[1-(4-iodophenyl)ethenyl]oxirane [34.3 g, 89 mmol, from step (e)] in dry DMF (350 ml) under nitrogen at 70° C. The mixture was stirred for 5 hours, cooled, and the solvent removed under reduced pressure. The residue was partitioned between ether (800 ml) and water (2×500 ml). The organic solution was dried (MgSO₄), filtered, and silica gel (60–200μ, 75 g) was added. The ether was removed under reduced pressure and the residual solid was applied to the top of a silica gel column (40–60μ, 300 g) and the product was eluted using hexane and increasing amounts of ethyl acetate (0–75%). The product was obtained as a white foam (23.8 g, 61%), which was characterised by $^1$H-N.M.R. spectroscopy.

(g) (R)-2-(2,4-Difluorophenyl)-3-(4-iodophenyl)-1-(1H-1,2,4-triazol-1-yl)-3-buten-2-ol (+)-3-bromocamphor-10-sulphonate A solution of (+)-3-bromocamphor-10-sulphonic acid (36.3 g, 0.110 moles) in IMS (40 ml) was added to a solution of the product of step (f) (50 g, 0.110 moles) in IMS (300 ml). After seeding, the resulting slurry was granulated for 20 hours at room temperature. A white solid (22 g, 0.03 moles) was collected by filtration after further granulating for 1 hour at low temperature. The chiral purity was assessed as 95% ee by chiral HPLC using a Chiralcel™ OD column and eluting with ethanol/hexane [40.60].

(h) (R)-2-(2,4-Difluorophenyl)-3-(4-iodophenyl)-1-(1H-1,2,4-triazol-1-yl)-3-buten-2-ol The product of step (g) (206.5 g, 0.27 moles) was added to methylene chloride (620 ml) and basified with 40% NaOH. The mixture was stirred for 15 minutes at room temperature and separated. The aqueous phase was re-extracted with methylene chloride (310 ml). The organic product solution was washed with water (620 ml) and concentrated to a volume of 245 ml. To the stirred and seeded concentrate at room temperature was added hexane (2450 ml) at a steady rate. The resulting slurry was granulated at 5° C. for 1 hour. Filtration afforded a white solid (117.4 g, 0.26 moles) which was characterized by $^1$H NMR spectroscopy.

(i) (2R)-2-(2,4-Difluorophenyl)-3-[4-(1-methylpyrazol-5-yl)phenyl]-1-(1,2,4-triazol-1-yl)-3-buten-2-ol nBuLi (1.6 N, 24.1 ml, 0.04 moles) was added to a solution of 1-methylpyrazole (3.28 g, 0.04 moles) in THF (370 ml) at −70° C. keeping the temperature below −60° C. and stirred for 30 minutes. Maintaining a temperature below −40° C., a solution of zinc chloride (0.5 N, 77.1 ml, 0.04 moles) was added, followed by palladium tetrakis (triphenylphosphine) (15% w/w, 0.9 g). Still keeping the temperature below −40° C., a solution of the product of step (h) (6 g, 0.013 moles) in THF (36 ml) was added at a steady rate. The reaction was allowed to warm to room temperature and then refluxed for 2 hours. After cooling to room temperature, the reaction was quenched with acetic acid (12 ml) and water (120 ml) keeping the temperature below 25° C. The reaction mixture was evaporated under reduced pressure to remove the THF. The product was extracted with methylene chloride (120 ml) and the aqueous phase further extracted with methylene chloride (50 ml). The combined organic extracts were washed with water (2×120 ml) and concentrated to give an oil. To a stirred filtered solution of the oil in ethyl acetate (100 ml) was added 5-sulphosalicylic acid (3.3 g, 0.13 moles) in IPA (10 ml). The resulting mixture was stirred at room temperature for ½ hour. The resulting filtered solid was repulped in ethyl acetate (50 ml) and recrystallized from IPA (60 ml) to afford a white solid (7.2 g, 0.01 moles). The solid was added to methylene chloride (35 ml) and water (50 ml) and basified with 40% NaOH. The mixture was stirred at room temperature for 15 minutes and separated. The aqueous phase was re-extracted with methylene chloride (25 ml) and the combined organic extracts washed with water (35 ml). The organic product solution was concentrated to a foam and characterized.

$[\alpha]_D$=−25.6°

$C_{22}H_{19}F_2N_5O.0.5$ H2O requires C, 63.45; H, 4.84; N, 16.82. Found C, 63.92; H, 4.86; N, 16.64.

(j) (2R,3S)-2-(2,4-Difluorophenyl)-3-[4-(1methylpyrazol-5yl)phenyl]-1-(1,2,4-triazol-1-yl)butan-2-ol

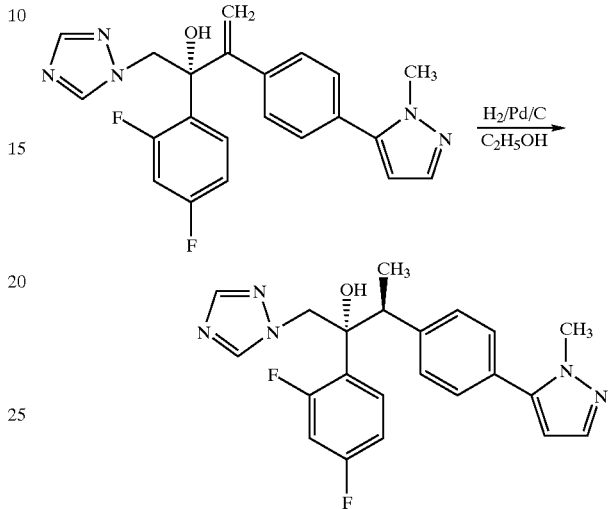

A solution of the product of step (i) (2.0 g, 5 mmol) in ethanol (S0 ml) was hydrogenated at 50 psi (333 KPa) pressure over 5% palladium on charcoal (0.2 g) for 18 hours at 50° C. A further batch of catalyst (0.2 g) was added, and the hydrogenation was continued for a further 18 hours. The mixture was filtered through Arbocel™ and the filtrate evaporated under reduced pressure. The residue was chromatographed on silica by gradient elution with ethyl acetate/hexane/diethylamine (0:95:5→65:33:2). Fractions containing the desired product were combined and evaporated under reduced pressure. The residue was dissolved and re-evaporated from ethyl acetate (×3) then from ether (×3) to yield a colourless solid. The solid was recrystallised from aqueous ethanol to give the subtitle compound (1.25 g, 62%) as a colourless solid, m.p. 144–145° C., $[\alpha]_D$=−107° (c=0.1%, $CH_2Cl_2$, 25° C.).

Elemental analysis (%) Found: C, 64.26; H, 5.13; N, 17.07. $C_{22}H_{21}F_2N_5O$ requires: C, 64.54; H, 5.17; N, 17.10.

(This compound is also disclosed as Example 67 in co-pending International Patent Application PCT/EP96/02470].

(k) Dibenzyl (2R,3S)-2-(2,4-difluorophenyl)-3-[4-(1-methylpyrazol-5-yl)phenyl]-1-(1,2,4-triazol-1-yl)-2-butyl phosphate

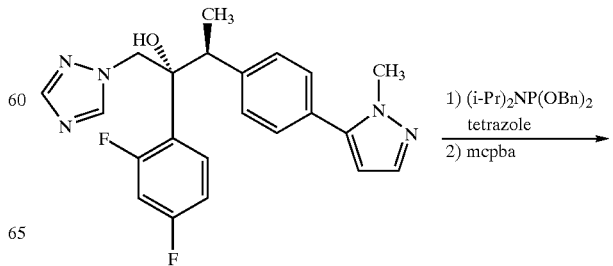

-continued

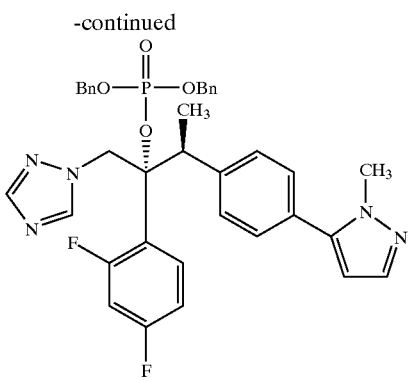

A solution of the product of step (j) (2.0 g, 4.4 mmol), dibenzyl diisopropylphosphoramidite (2.28 g, 6.6 mmol), tetrazole (0.92 g, 13.2 mmol) and 4-dimethylaminopyridine (50 mg) in dichloromethane (30 ml) was heated under reflux for 13 hours. The reaction mixture was cooled (0° C.) and m-chloroperbenzoic acid (1.52 g, 8.8 mmol) added. The solution was stirred at 0° C. for a further hour then allowed to warm to room temperature. The reaction mixture was washed with aqueous sodium sulphite solution (10%, 30 ml), saturated sodium bicarbonate solution (30 ml) and brine (30 ml). The organic layer was dried ($Na_2SO_4$) and solvent was evaporated in vacuo to give an oil. Purification by column chromatography (silica gel, 45 g, eluting with toluene to 3.5% diethylamine in toluene gradient) gave the required product as a colourless oil (0.8 g, 27%), m/z 671 ($M^+$+1). $^1$H N.M.R. ($CDCl_3$) δ=1.3 (d, 3H); 3.8 (s, 3H); 3.85 (q, 1H); 4.8 (m, 2H); 4.9 (m, 2H); 5.2 (s, 2H); 6.25 (s, 1H); 6.6 (m, 1H); 6.8 (m, 1H); 7.05 (m, 1H); 7.15 (m, 2H); 7.2–7.35 (m, 12H); 7.5 (s, 1H); 7.8 (s, 1H); 8.23 (s, 1H).

(l) (2R,3S)-2-(2,4-Difluorophenyl)-3-[4-(1-methylpyrazol-5-yl)phenyl]-1-(1,2,4-triazol-1-yl)-2-butyl disodium phosphate

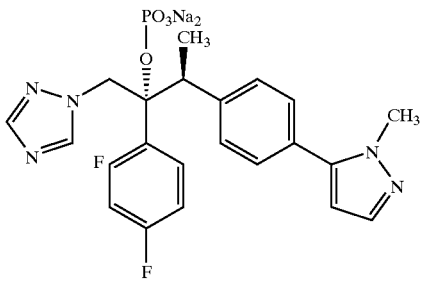

A suspension of the product of step (k) (0.5 g, 0.75 mmol) and sodium acetate (0.14 g, 1.65 mmol) in ethanol (20 ml) was hydrogenated over 5% Palladium on carbon (75 mg) at room temperature and 333 KPa (50 p.s.i.) for 24 hours. Tlc analysis showed incomplete reaction and the catalyst was filtered off through a pad of filter aid (Arbacel, trade mark). Pearlman's catalyst (75 mg) was then added and hydrogenation continued for a further 72 hours. The catalyst was filtered off through a pad of Arbacel and solvent removed in vacuo. The residue was dissolved in dichloromethane (20 ml) and filtered through a pad of filter aid (Hiflow, trade mark) to remove excess sodium acetate. Solvent was evaporated in vacuo and after trituration with diethyl ether, the title compound obtained as a white solid (0.250 g, 68%). Found: C, 46.65; H, 4.87; N, 11.82; $C_{22}H_{22}F_2N_5Na_2O_4P$. 0.09 $Et_2O$ requires C, 46.62; H, 4.36; N, 12.16%. $^1$H N.M.R. (DMSO) δ=1.2 (d, 3H); 3.75 (q, 1H); 3.8 (s, 3H); 5.1, 5.5 (AB system, 2H); 6.3 (s, 1H); 6.6 (m, 1H); 6.9 (m, 1H); 7.2, 7.4 (AB system, 4H); 7.4 (m, 3H); 7.45 (m, 1H); 7.6 (s, 1H); 9.1 (s, 1H).

EXAMPLE 9

The aqueous solubilities of the compounds of Examples 1, 3 and 8 (in the form or their disodium salts) were compared with the solubilities of their respective parent (non-phosphorylated) compounds (in free base form). The results are shown in the following table.

| Compound | Solubility (mg/ml) |
| --- | --- |
| Example 1 | >150 |
| Parent | 2 |
| Example 3 | >150 |
| Parent | 0.6 |
| Example 8 | >50 |
| Parent | 0.01 |

EXAMPLE 10

Aqueous Formulation for i.v. Injection

| Ingredient | mg/ml |
| --- | --- |
| Compound of Example 1 | 100.00 |
| Sodium hydroxide | 22.80 |
| Hydrochloric acid, concentrated | q.s.* |
| Water for injections | to 1.00 ml |

*The pH range of the resulting solution is adjusted to between pH 8.5 and 9.5 by the addition of a sufficient quantity of 5M hydrochloric acid.

What is claimed is:

1. A compound which is: 2-(2,4-difluorophenyl)-1,3-bis(1H-1,2,4-triazol-1-yl)-2-propyl dihydrogen phosphate; or a pharmaceutically acceptable salt thereof.

2. A compound which is: Alkali metal salt of 2-(2,4-difluorophenyl)-1,3-bis(1H-1,2,4-triazol-1yl)-2-propyl dihydrogen phosphate.

3. A compound which is: 2-(2,4-difluorophenyl)-1,3-bis(1H-1,2,4-triazol-1-yl)-2-propyl disodium phosphate.

* * * * *